United States Patent [19]

Bachynsky

[11] Patent Number: 4,673,691

[45] Date of Patent: Jun. 16, 1987

[54] HUMAN WEIGHT LOSS INDUCING METHOD

[75] Inventor: Nicholas Bachynsky, 1110 Pine Cir., Sea Brook, Tex. 77586

[73] Assignee: Nicholas Bachynsky, Sea Brook, Tex.

[21] Appl. No.: 668,501

[22] Filed: Nov. 5, 1984

[51] Int. Cl.[4] ............................................ A61K 31/195
[52] U.S. Cl. ..................................... 514/567; 514/909
[58] Field of Search ......................... 514/728, 909, 567

[56] References Cited

U.S. PATENT DOCUMENTS 4,087,554  5/1978  Haydock et al. .................... 514/728

OTHER PUBLICATIONS

Chem. Abst. 66:82758c (1967)—Rossini et al.
Chem. Abst. 71:27671x (1969)—Tomita et al.
Chem. Abst. 77:109780v (1972)—Tiller et al.
Chem. Abst. 82:25791q (1975)—Wahl et al.
Chem. Abst. 88:167300b (1978)—Kaplan et al.
Chem. Abst. 89:191455x (1978)—Organesyan et al.
Chem. Abst. 100:168805y (1984)—Sydykov.
Chem. Abst. 102:56608w (1985)—Langer.
Simkins, S., "Dinitrophenol and Desiccated Thyroid in the Treatment of Obesity," JAMA 108, pp. 2110-2117 and 2193-2199 (1937).
Tainter, M. L. et al., "Dinitrophenol in the Treatment of Obesity," JAMA 105, pp. 332-336 (1935).
Tiller, F. W. et al., "The Effects of Noradrenaline and 2,4-Dinitrophenol on the Oxygen Consumption of Different-Aged Rats After Treatment with Triiodothyronine or Methylthiouracil," Arch. Int. Pharmacodyn. 198, pp. 377-384 (1972) (With Translation).
Wahl, R. et al., "Influence of Various Drugs on the Adsorption of Thyroid Hormones to Liver Mitochondria," Z. Naturforsch, 29, pp. 608-617 (1974) (With Translation).
Schimmel, M. et al., "Thyroidal and Peripheral Production of Thyroid Hormones," Annals of Internal Medicine 87, pp. 760-768 (1977).
Arena, Jay M., Poisoning, pp. 86 and 92 (Charles C. Thomas, Springfield, Ill. (1978).
Cazeneuve, P. et al., "Sur les effets produits par l'ingestion et l'infusion intra-veineuse de trois colorants jaunes, derives de la houille," C.R. Acad. Sci. 101, pp. 1167-1169 (1885).
Brobeck, J. R., "Food Intake as a Mechanism of Temperature Regulation," Yale Journal of Biology and Medicine 20, pp. 545-552 (1948).
Cutting, W. C. et al., "Actions and Uses of Dinitrophenol," JAMA 101, pp. 193-195 (1933).
Diechmann, W. B. et al., Symptomatology and Therapy of Toxicological Emergencies, pp. 452-453 (Academic Press, New York 1964).
Counsel on Pharmacy and Chemistry, "Dinitrophenol Not Acceptable for N.N.R.," JAMA 105, pp. 31-33 (1935).
Horner, W. D., "Cataract Following Dinitrophenol Treatment for Obesity," Archives of Opthalmology 16, pp. 447-461 (1936).
Negherbon, W. O., Handbook of Toxicology, vol. 3, pp. 303-308, (W. B. Saunders Co., Philadelphia 1959).
Perkins, R. G. "A Study of the Munitions Intoxications in France," Public Health Reports 34, pp. 2335-2374 (1919).
Sims, E. A. H. et al., "Endocrine and Metabolic Effects of Experimental Obesity in Man," Recent Progress in Hormone Research 29, pp. 457-496 (1973).
Spector, W. S., Handbook of Toxicology, vol. 1, p. 118, (W. B. Saunders Co., Philadelphia, 1956).
Tainter, M. L. et al., "A Case of Fatal Dinitrophenol Poisoning," JAMA 102, pp. 1147-1149 (1934).
Physician's Desk Reference, 37th ed., pp. 1896-1897 (1983).

*Primary Examiner*—Douglas W. Robinson
*Attorney, Agent, or Firm*—Pravel, Gambrell, Hewitt & Kimball

[57] ABSTRACT

A human weight reduction method in which 2,4-dinitrophenol and a thyroid hormone preparation are administered to the patient. The dinitrophenol is administered in dosages sufficient to elevate the patient's body temperature, typically 250 mg every other day. The thyroid hormone preparation preferably contains 3,5,3'-triiodothyronine and is administered in dosages sufficient to substantially maintain the patient's serum T3 concentration originally present at treatment onset.

8 Claims, No Drawings

HUMAN WEIGHT LOSS INDUCING METHOD

This invention relates to a method of inducing weight loss in patients by the concurrent administration of 2,4-dinitrophenol and 3,5,3'-triiodothyronine.

BACKGROUND OF THE INVENTION

Obesity is a common problem. Simply stated, obesity is an excess accumulation of adipose tissue which contains fat stored in the form of triglycerides. The number of cells in the body is determined at least by late adolescence and while the number of adipocyte cells may increase, it does not decrease. Thus, weight gain can result from an enlargement of adipocyte cells or an increase in their number. Typically, obese individuals have hypertrophic cells and the severely obese have an increase in adipose cell number as well as hypertrophy. An obese patient only reduces the fat in his cells when he loses weight. Further, he may not ever lose the tendency to gain weight.

Body weight is regulated by an endogenous body mechanism. Physiological and neurological properties establish and maintain a given weight. Briefly stated, glycerol which is released during hydrolysis of triglycerides and adipose tissue is widely believed to regulate caloric intake and metabolism. Others have postulated that caloric intake is affected by both body temperature and environmental temperature. In addition, cell size and number affect energy regulation. Weight gain cannot be predicted solely on the amount of calories ingested.

In normal persons, thermogenesis is an adaptive mechanism which increases the metabolic rate after overeating. While a normal person will experience an increase in thermogenesis following increased caloric intake, the obese either has a substantially decreased thermogenic mechanism or lacks this particular mechanism entirely.

The use of dinitrophenol to treat obesity is known. Dinitrophenol is known to elevate the body temperature and produces a marked increase in caloric metabolism. However, ingestion of massive amounts of dinitrophenol causes toxicity by the uncoupling of oxidative phosphorylation in the mitochondria of cells. Because of this toxicity, excessive amounts can result in profuse diaphoresis, fever, thirst, tachycardia and respiratory distress which can lead to hyperpyrexia, profound weight loss, respiratory failure and death. The minimum fatal human oral dose is estimated at one to three grams (approximately 20–30 mg/kg).

In methods heretofore known to using dinitrophenol to induce weight loss, while initial daily dosages have usually been much less than the toxic amount, about 100–250 mg, as the treatment progressed the patient normally developed a tolerance for dinitrophenol and the dosage was increased to obtain the same results. This increased dosage led to an increased frequency of toxic symptoms and general disuse of dinitrophenol in inducing weight loss.

It has also been known to use drugs with thyroid hormone activity for the treatment of obesity. However, as described in *Physicians' Desk Reference*, Medical Economics Co. Inc., (Oradell, N.J.), 37th Ed. (1983), in euthyroid patients, it is well established that doses within the daily hormonal requirements are ineffective for weight reduction. However, larger doses may produce serious or even life-threatening manifestations of toxicity.

SUMMARY OF THE INVENTION

The present invention avoids the necessity of increased dosages of dinitrophenol and the concomitant toxicity problems associated therewith as treatment progresses while obtaining improved results. It has been discovered that the use of dinitrophenol induces hypothyroidism which can be prevented by concurrently administering thyroid hormone preparation with the dinitrophenol.

Briefly, the present invention is a method of inducing weight loss in patients, including the steps of administering dinitrophenol to the patient in an amount sufficient to clinically increase thermogenesis of the patient, and concurrently administering a thyroid hormone preparation to the patient in an amount sufficient to substantially maintain the serum concentration of 3,5,3'-triiodothyronine of the patient originally present at treatment onset.

DETAILED DESCRIPTION OF THE PREFERRED EMBODIMENT

It has been discovered that the ingestion of dinitrophenol induces hypothyroidism. Athough it is not fully understood, it is believed that the normal thyroid gland produces both thyroxine (referred to herein as T4) and 3,5,3'-triiodothyronine (referred to herein as T3). However, approximately eighty percent of the serum T3 present in the body is produced by the extrathyroidal monodeiodination of T4 to T3. When dosages of dinitrophenol are taken, hypothyroidism is induced, not by a reduction in activity of the thyroid, but by a reduction of the rate of extrathyroidal conversion of T4 to T3. While both T4 and T3 are biologically active, T3 is much more active than T4. Thus, the reduction in serum T3 concentration induced by taking dinitrophenol substantially offsets the metabolic effect of the dinitrophenol. By analogy, the reduction in serum T3 concentration is similar to that observed in fasting patients. Typically, normal serum T3 concentration ranges from about 70 to about 200 ng/dl.

It has further been discovered that deficient serum T3 concentrations resulting from administration of dinitrophenol can be restored to normal concentrations by concurrently administering a thyroid hormone preparation therewith.

In practicing the method of this invention, dinitrophenol is administered to the patient. The metabolically active dinitrophenols suitable for use in the invention include 2,4-dinitrophenol and the salts thereof. By the term administration is meant any suitable manner of introducing the medication into the patient's body, including orally (p.o.) and topically. The preferred manner of administering dinitrophenol is orally, as in the form of a tablet or capsule.

The amount of dinitrophenol given should be sufficient so that the patient experiences increased body temperature. Preferably, the body temperature is elevated approximately 1° F. The dose of dinitrophenol required to obtain this result varies from patient to patient, depending on factors such as, for example, weight, age, health, environmental conditions, physical activity, nutrition, and psychological state, but will normally be in the range of from about 60 to about 500 mg per day, or about 0.60 to about 5.0 mg/kg of body weight per day. Preferably, the dinitrophenol is administered in daily or alternating daily dosages, insuring that no cumulative effective results, such as excessive thermogenesis.

It is essential that the amount of dinitrophenol administered not exceed toxic doses. In a few patients, adverse reactions may occur at dosages of dinitrophenol which are not effective to elevate the body temperature, contraindications including any clinical state in which there is hypermetabolism, such as hyperthyroidism, ongoing infections, and pregnancy, and any other clinical conditions such as heart disease, chronic obstructive pulmonary disease, Addison's disease, liver disorders, or renal failure. Most are safely treated with suitable results from the aforementioned dosages.

Concurrently with the administering of the dinitrophenol, or shortly thereafter, a thyroid hormone preparation is administered to the patient. As used herein, the term thyroid hormone preparation includes any suitable preparation which restores the serum T3 concentration, including preparations containing 3,5,3'-triiodothyronine, thyroxine, derivatives thereof or combinations thereof. Preferably, the thyroid hormone preparation contains T3. Because of the varying potency of such preparations, dosages of thyroid harmone preparation are reported herein on a T3 equivalent basis.

The thyroid hormone preparation is administered in an amount sufficient to maintain the pretreatment serum T3 concentration in the patient, typically about 70–200 ng/dl in normal patients. Generally, from about 25 to about 200 mcg T3 equivalent per day, or from about 0.3 to about 2.7 mcg T3 equivalent per kilogram of body weight per day, is sufficient. Preferably, the thyroid hormone preparation is administered daily. In an especially preferred embodiment, the thyroid hormone preparation is administered orally with the dinitrophenol.

As described above, the rate of extrathyroidal conversion of T4 to T3 may vary as treatment with the dinitrophenol progresses. Thus, it may be necessary to increse or decrease the dosage of the thyroid hormone preparation accordingly.

It is preferred that in the practice of the method of this invention, the patient be closely monitored, especially in the initial stages of treatment. Recommended pretreatment and initial treatment protocol includes physical examination, electrocardiogram, and stress electrocardiogram if indicated, complete blood count, urinalysis, thyroid function studies (T3, T4 and reverse T3), serum electrolytes, HDL cholesterol, serum creatinine, blood urea nitrogen, uric acid, calcium, pulmonary function tests and liver function tests including liver enzymes, biliribin, and alkaline phosphatase.

In an especially preferred embodiment, the patient is started on initially lower dosage rates of dinitrophenol, about 250 mg every other day, and thyroid hormone preparation, about 25–50 mcg/day on a T3 equivalent basis. After 2–12 weeks of this treatment, if no adverse reactions are noted, the dosage rates may be increased to about 250 mg dinitrophenol alternated daily with about 125 mg, i.e. 250 mg on even-numbered days and 125 mg on odd-numbered days, and to about 100 mcg/day thyroid hormone preparation on a T3 equivalent basis. When the weight goal of the patient is achieved, the administration of the dinitrophenol may be discontinued, and the thyroid hormone preparation continued to maintain the patient's weight. While dietary control need not be strict, weight loss and weight maintenance are facilitated by moderate caloric intake of less than about 1800 calories per day, during and following treatment.

This method is illustrated by way of the case histories which follow.

Case 1

A white female 31 years of age with a weight in excess of 200 pounds had attempted to loss weight with various diet plans. She had only been able to achieve about a 20-pound loss, and had immediately regained the weight. The patient was nulliparous and had no ongoing medical problems. Upon physical examination, she had a weight of 208.5 pounds, a height of 5 feet, 3 inches, and a blood pressure of 132/80, without any goiter. Laboratory analyses, including complete blood count, liver profile, serum electrolytes, kidney function tests and thyroid function tests, were all within normal limits. Because of her familial history of heart disease, she underwent a stress electrocardiogram which was normal other than early fatigue and calf cramping.

The patient was started on CYTOMEL brand of liothyronine sodium (manufactured by Smith, Kline and French), 50 mcg/day p.o., and on 2,4-dinitrophenol, 250 mg every other day p.o. On the 19th day of medication, the patient had normal vital signs and the dosages were increased to 100 mcg/day liothyronine, and 250 mg/day dinitrophenol alternated every other day with 125 mg/day. The patient was subsequently maintained on these dosages and returned for follow-up examinations approximately every 3 weeks. The weight loss history is seen in Table 1. After 241 days of medication, the patient has achieved her weight goal of 135 pounds. Administration of the dinitrophenol was discontinued and the patient was maintained on liothyronine, 100 mcg/day p.o. No weight gain was subsequently observed.

TABLE 1

| Day | Weight (lbs) |
| --- | --- |
| 1 | 208½ |
| 19 | 202½ |
| 35 | 196½ |
| 49 | 189½ |
| 69 | 184 |
| 92 | 175 |
| 113 | 167 |
| 134 | 160 |
| 155 | 152½ |
| 180 | 148 |
| 206 | 146 |
| 241 | 135 |

Case 2

A male 40 years of age with a weight of approximately 250 pounds had attempted to lose weight with a variety of diet plans and diet medications. Success had been limited to 5–10 pound weight losses, with immediate regain. On physical examination, the patient has a height of 5 feet, 10 inches, a weight of 255 pounds and a blood pressure of 160/100. Complete blood count, SMAC, serum electrolytes, thyroid function tests, glucose tolerance tests and stress electrocardiogram were normal.

The patient was started on liothyronine, 50 mcg/day p.o., and on dinitrophenol, 250 mg every other day p.o. After two weeks, the blood pressure returned to normal (130/80), and the dosages were increased to 100 mcg/day liothyronine and 250 mg dinitrophenol alternated daily with 125 mg. The weight loss history is presented in Table 2. Once the weight goal of 167 pounds had been achieved, the patient was taken off the dinitrophenol administration and the 100 mcg/day liothyronine medication was maintained. The patient was instructed to restrict caloric intake to approximately 1800 calories per day. No subsequent weight gain was observed.

TABLE 2

| Day | Weight (lbs) |
| --- | --- |
| 1 | 255 |
| 14 | 241 |
| 30 | 232 |
| 44 | 227 |
| 65 | 220 |
| 76 | 214 |
| 97 | 208 |
| 125 | 203 |
| 153 | 197¾ |
| 181 | 193 |
| 209 | 189 |
| 279 | 178 |
| 321 | 167 |

Case 3

A white male 38 years of age with a weight of approximately 342 pounds had made numerous attempts to lose weight "with all methods" without any success. Upon physical examination, the patient had a weight of 352 pounds, a height of 5 feet, 11 inches and a blood pressure of 150/110. Other than a slight enlargement of the heart on X-ray and +3 pitting edema, the physical examination was unremarkable. Laboratory analysis initially revealed a blood sugar of 372 with a glycohemoglobin of 14.3 (normal 4.4–8.2). The remaining tests, including stress electrocardiogram, were within normal limits. The patient was started on liothyronine, 50 mcg/day p.o., and dinitrophenol, 250 mg every other day, and was instructed to restrict his caloric intake to approximately 1800 calories per day. On the 59th day of treatment, the dosages were increased to 100 mcg/day liothyronine, and 250 mg/day dinitrophenol alternated every day with 125 mg. The patient's weight loss history is presented in Table 3. Following treatment, the dinitrophenol administration was discontinued and the patient was maintained on liothyronine, 100 mcg/day p.o. and instructed to maintain his caloric intake to approximately 1800 calories per day. No subsequent weight gain was observed.

TABLE 3

| Day | Weight (lbs) |
| --- | --- |
| 1 | 354 |
| 24 | 333 |
| 38 | 314 |
| 59 | 317 |
| 80 | 297¼ |
| 101 | 288 |
| 122 | 275 |
| 143 | 260½ |

TABLE 3-continued

| Day | Weight (lbs) |
| --- | --- |
| 164 | 254 |
| 185 | 243½ |
| 206 | 246 |
| 227 | 235½ |
| 248 | 234 |
| 269 | 229 |
| 290 | 222 |

The above cases illustrate the effectiveness of the method with obese patients unable to reduced their weight by conventional methods.

Having described any weight loss method above, many variations in the details thereof will occur to those skilled in the art. It is intended that all such variations which fall within the scope and spirit of the appended claims be embraced thereby.

I claim:

1. A method of inducing weight loss in a patient, comprising the steps of:
   (a) administering 2,4-dinitrophenol or salt thereof at a rate ranging from about 60 to about 250 mg/day; and
   (b) concurrently administering 3,5,3'-triiodothyronine to the patient at a rate ranging from about 25 to about 100 mcg/day.

2. The method of claim 1, wherein said 3,5,3'-triiodothyronine is substantially free of thyroxine.

3. The method of claim 1, wherein said 3,5,3'-triiodothyronine administration is at a rate ranging from about 50 to about 100 mcg/day.

4. The method of claim 1, wherein said dinitrophenol is administered at said rate with dosages given only on alternate days.

5. The method of claim 1, wherein said dinitrophenol is administered at said rate with primary dosages given on alternate days and smaller, supplemental dosages given on the days immediately subequent to said alternate days.

6. The method of claim 1, wherein 2,4-dinitrophenol is administered.

7. A method of inducing weight loss in a patient, comprising the steps of:
   (a) administering 2,4-dinitrophenol to the patient at a rate ranging from about 125 to about 250 mg/day; and
   (b) concurrently administering 3,5,3'-triiodothyronine substantially free of thyroxine to the patient at a rate ranging from about 50 to about 100 mcg/day.

8. The method of claim 7, wherein said dinitrophenol and said 3,5,3'-triiodothyronine are administered at initial rates of about 250 mg of said dinitrophenol every other day and about 50 mcg 3,5,3'-triiodothyronine per day, and following 2–12 weeks of said administration at said initial rates, are administered at subsequent rates of about 250 mg of said dinitrophenol every other day alternated with about 125 mg of said dinitrophenol on subsequent days and about 100 mcg 3,5,3'-triiodothyronine per day.

* * * * *